United States Patent [19]
Benchetrit

[11] Patent Number: 5,681,342
[45] Date of Patent: Oct. 28, 1997

[54] DEVICE AND METHOD FOR LAPAROSCOPIC INGUINAL HERNIA REPAIR

[76] Inventor: Salomon Benchetrit, 276 rue André Philip 69003, Lyon, France

[21] Appl. No.: 516,455

[22] Filed: Aug. 17, 1995

[51] Int. Cl.⁶ ................................................. A61M 29/00
[52] U.S. Cl. ............................................ 606/192; 600/207
[58] Field of Search ................................. 600/201, 204, 600/205, 206, 207, 208; 606/190, 191, 192, 185; 604/264, 96, 167, 164

[56] References Cited

U.S. PATENT DOCUMENTS

| | | | |
|---|---|---|---|
| 4,798,586 | 1/1989 | Stevens | 604/96 |
| 4,932,959 | 6/1990 | Horzewski et al. | 604/96 |
| 5,066,285 | 11/1991 | Hillstead | 604/264 |
| 5,197,955 | 3/1993 | Stephens et al. | 604/167 |
| 5,226,889 | 7/1993 | Sheiban | 604/264 |
| 5,258,003 | 11/1993 | Ciaglia et al. | 604/264 |
| 5,330,437 | 7/1994 | Durman | 604/167 |
| 5,331,975 | 7/1994 | Bonutti | 606/192 |
| 5,439,476 | 8/1995 | Frantzides | 600/207 |
| 5,445,624 | 8/1995 | Jimenez | 604/280 |
| 5,514,153 | 5/1996 | Bonutti | 606/190 |

FOREIGN PATENT DOCUMENTS 0 573 273 A2  12/1993  European Pat. Off. .

*Primary Examiner*—Michael Buiz
*Assistant Examiner*—Patrick W. Rasche
*Attorney, Agent, or Firm*—Nikaido, Marmelstein, Murray & Oram LLP

[57] ABSTRACT

A laparoscopic surgical separating device (1) for creating a preperitoneal workspace, for use in preperitoneal laparoscopic inguinal hernia repair, comprising a relatively rigid longitudinal element (2), a longitudinal axis (5), an interior wall (6) defining a throughbore (7), an inflatable element (8) fixedly attached to a point (9) along the length of an outer wall (10) of element (2), fluid insufflation member (11), connected to inflatable element (8), and to throughbore (7), and sealing member (12) capable of preventing fluid from escaping from element (2), wherein inflatable element (8) is of generally asymmetrical shape, having, on one side of the axis (5), a relatively large portion (13) of inflatable material, and on the other side of the axis (5) in the same plane, a relatively small portion (15) of inflatable material, the portions (13, 15) corresponding to the space available in the body after insertion and inflation of the device (1) via an incision (16) made at the antero-superior iliac crest (17).

17 Claims, 4 Drawing Sheets

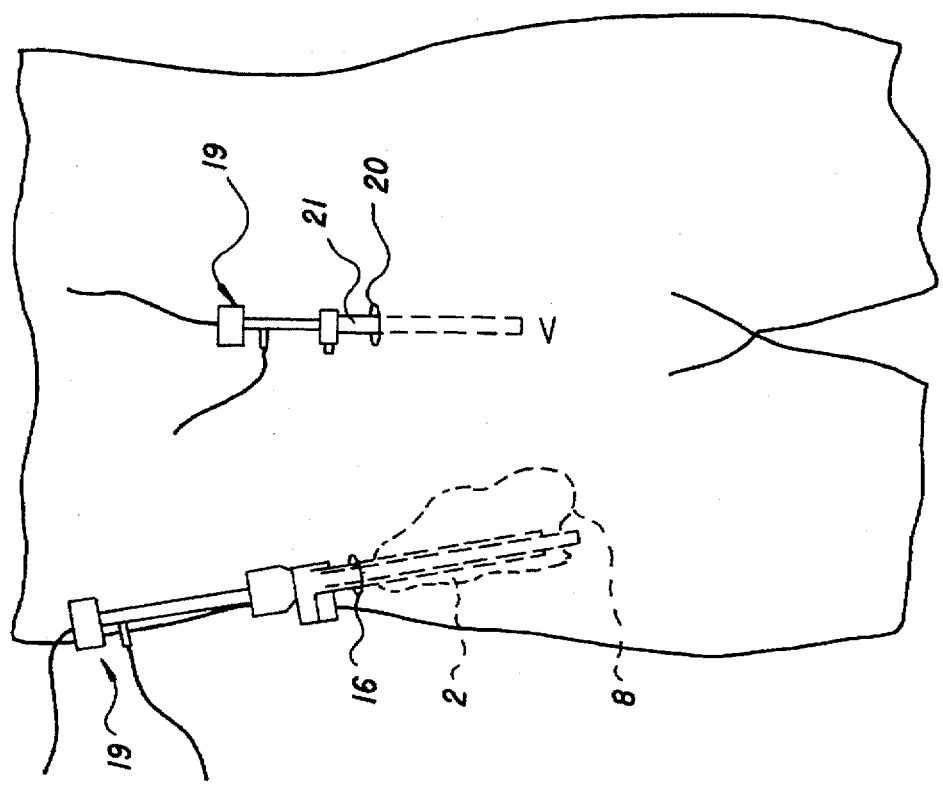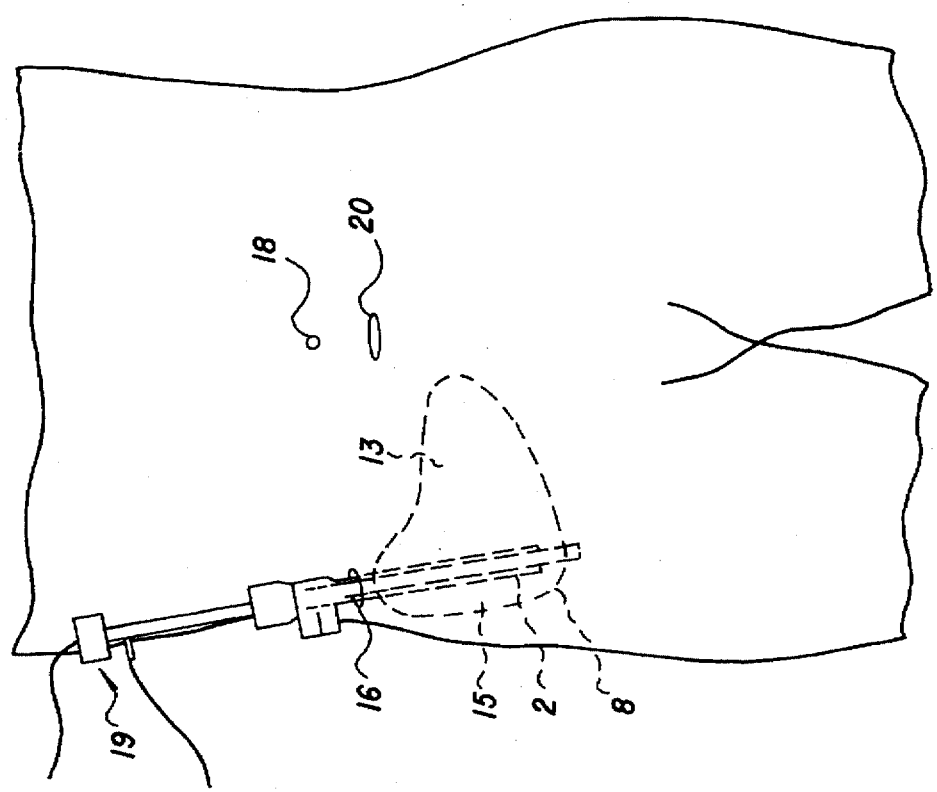

1

DEVICE AND METHOD FOR LAPAROSCOPIC INGUINAL HERNIA REPAIR

BACKGROUND TO THE INVENTION

The present invention concerns a device used in laparoscopic surgery, in particular, laparoscopic inguinal hernia repair surgery, and a method of carrying out such surgical repair.

Laparoscopic or keyhole surgical interventions have recently taken on increasing importance as surgeons have realized the benefits, both in terms of cost and patient comfort, of minimal invasive surgical techniques. Accordingly, there has been a constant development in the techniques used in this type of surgery and the equipment necessary to successfully carry out such operations.

In the particular field of hernia repair, the application of preperitoneal laparoscopic techniques has enabled surgeons to obviate many of the dangers of traditional open bowel surgery, and even intraperitoneal laparoscopy, since the technique does not involve the risk of the surgeon damaging a sensitive organ with one of the inserted instruments. The basis for this technique lies in separating two layers of tissue, namely the peritoneum from the overlying abdominal wall, and creating a sufficiently large working preperitoneal space therebetween to enable the surgeon to carry out the hernia repair.

At present, and for inguinal hernia repair, the operative procedure is the following. Such a procedure is known from EP-A-0 573 273, the disclosure of which is hereby incorporated by reference for the teachings of such procedure therein.

After anaesthetization and preparation of the patient, a first incision is made infra-umbilically in the skin below the navel or umbilicus, the fat layer is separated, and the incision continued through to the anterior surface of the posterior rectus sheath in the midline. A separating device is introduced laterally between the peritoneum and the rectus muscles, and tunnelled toward the symphysis pubis.

This device generally comprises at least one relatively rigid longitudinal element having distal and proximal ends, defining a longitudinal axis, the interior wall of which defines at least one throughbore, an symmetrical inflatable element fixedly attached to at least one point along the length of the outer wall of said longitudinal element, fluid insufflation means connecting with the inflatable element and capable of inflating said element, and via the at least one throughbore, enabling creation of a pneumoperitoneum in the preperitoneal cavity formed by the separation of said peritoneum and said overlying abdominal wall, when fluid is insufflated therethrough, and sealing means capable of preventing the insufflated fluid from escaping via the proximal end of the relatively rigid longitudinal element.

This device is advanced to preferably be disposed between the bladder and the symphysis pubis by tunnelling as mentioned previously. Once in position, the symmetrical inflatable element, which before deployment is in a rolled up configuration, is inflated with fluid. The inflatable element progressively unwraps equally from both sides of the longitudinal element and expands along a plane to cause progressive separation or dissection of tissue along its weakest points by application of forces generally perpendicular to the plane of the inflatable element, thereby creating a preperitoneal space. When complete inflation is achieved, the inflatable element is deflated, withdrawn and replaced by a conventional laparoscope. The dissected preperitoneal space is then insufflated with carbon dioxide via the insufflation means, and two additional trocars are inserted through the abdominal wall into the dissected preperitoneal workspace, one immediately above the symphysis pubis, and the other to the left or right side of the abdomen depending on the site of the hernia to be repaired.

Subsequently, the hernial sac is dissected from the surrounding tissue, in particular, the spermatic duct and vessels, and a hernia repair prosthesis, generally in the form of a synthetic patch or graft, is placed across the inguinal ring and around said vessels and stapled to keep it in place. The preperitoneal workspace is then deflated, by release of the insufflated carbon dioxide, under laparoscopic observation, and the instruments withdrawn. At the same time, the abdominal wall and peritoneum return to their initial position, the original incisions necessitating only small sutures with consequently limited scarring.

The major disadvantage of the above method and device is related to the tunnelling step. Indeed, the traumatic character of the technique is dependent on the careful manipulation of the device by the surgeon during the tunnelling step. If this step is carried out hurriedly, it is likely that the device will puncture or tear through the underlying peritoneum, risking damage to an organ of the body, or at least traumatising the peritoneum. Consequently, an atraumatic tunnelling is necessarily very time consuming and fastidious.

SUMMARY OF THE INVENTION

It is an object of the present invention to overcome the disadvantages of the prior art by providing a device and surgical method enabling a relatively rapid atraumatic separation of the peritoneum from the overlying abdominal wall, without the need for the potentially dangerous tunnelling step, thereby facilitating the surgeon's task.

It is therefore an object of the invention to provide a laparoscopic surgical separating device adapted to separate the peritoneum from the overlying abdominal wall, thereby permitting access to a preperitoneal operative site, for use in preperitoneal laparoscopic inguinal hernia repair, comprising at least one relatively rigid longitudinal element having distal and proximal ends, defining a longitudinal axis, the interior wall of which defines at least one throughbore, an inflatable element tightly surrounding at least a distal part of the outer or interior walls of said at least one longitudinal element, inflating means communicating with the inflatable element and capable of inflating said element, wherein the inflatable element can adopt a first, flattened deflated configuration for its introduction, and a second, substantially planar inflated configuration along a median plane to provide a separating force perpendicular to said median plane when the inflatable element is inflated, thereby enabling the separation of the peritoneum and the overlying abdominal wall to create a preperitoneal workspace, the inflatable element being disposed around said longitudinal axis, and along said at least longitudinal element over a predetermined distance, wherein said inflatable element has a generally asymmetrical shape, which shape is defined by the element having, on one side of said axis, a relatively large and substantially flat surface area, and on the other side of said axis, a relatively small substantially flat surface area, whereby said surface areas correspond to the space available in the body after insertion of the device via an incision made at the antero-superior iliac crest.

It is a further object of the invention to provide a method for separating the peritoneum from an overlying abdominal wall and creating a preperitoneal workspace permitting access to a preperitoneal operative site, comprising:

(a) making a first traversing incision in the abdominal walls far as the anterior surface of the peritoneum, in the vicinity of an antero-superior iliac crest, homolateral to the hernia to be repaired;

(b) introducing a separating device horizontally into the incision thus made, thereby entering the preperitoneal region;

(c) causing the device to expand more towards the opposite facing side of the body than to the side of introduction, whereby separation of the peritoneum from the overlying abdominal wall is achieved by the effect of an expanding force acting perpendicular to a plane of separation between said peritoneum and said overlying abdominal wall, thereby creating a preperitoneal cavity;

(d) causing the device to contract, and insufflating the preperitoneal cavity with insufflating fluid to create a preperitoneal pneumoperitoneum, thereby creating an operative workspace.

Furthermore, it is another object of the present invention to provide a method for repairing inguinal hernias laparoscopically comprising carrying out previously described steps (a) to (d), wherein the method further comprises:

(e) making a second traversing incision infra-umbilically, through the anterior rectus sheath, and retracting the rectus abdominis muscles;

(f) introducing a trocar equipped with a laparoscope via said second incision into the preperitoneal workspace created;

(g) introducing a third trocar into the preperitoneal workspace above the symphysis pubis;

(h) dissecting and reducing the hernia, and placing a repairing prosthetic patch at the site thereof.

Indeed, the approach used in the method for placing the device of the present invention is advantageous in that the separation of the peritoneum by the device from the overlying abdominal wall is easily commenced due to the relatively small thickness of the abdominal wall at the point of first incision, i.e. in the vicinity of the antero-superior iliac crest. Furthermore, the inflatable element of the device substantially corresponds to the anatomically available space in the preperitoneal region, and the intervention can be carried out reproducibly and reliably with a significantly reduced number of manipulations, as only one device is involved, thereby reducing the risk of traumatising the peritoneum or the abdominal wall.

These and other objects and advantages of the present invention will be more clearly understood by the following detailed description, with reference to the following annexed drawings.

DESCRIPTION OF THE FIGURES

FIG. 3 represents the same schematic view as FIG. 2, after introduction, via the first incision, of the device depicted in FIG. 1, and inflation of the inflatable element.

FIG. 4 represents the same views as FIGS. 2 and 3, subsequent to deflation of the inflatable element, insufflation of the preperitoneal cavity, and the making of a second incision through which a second laparoscopic instrument is inserted into the created preperitoneal workspace.

PREFERRED EMBODIMENTS OF THE INVENTION

The device of the invention, as introduced previously, is designed to be used in laparoscopic surgical interventions, and in particular in inguinal hernia repair via the preperitoneal approach, for separating the peritoneum from an overlying abdominal wall.

Figure 1:
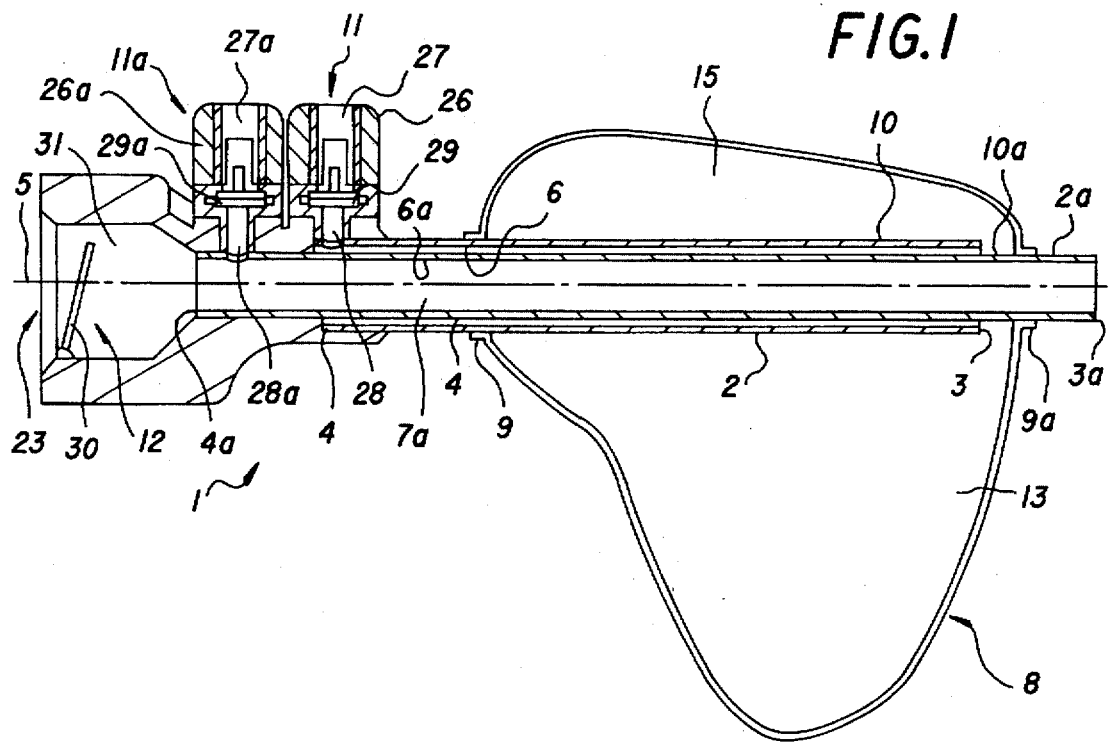
FIG. 1 represents a longitudinal cross section of a preferred device according to the present invention.

In a first preferred embodiment, and as shown schematically in the longitudinal cross section of FIG. 1, the device comprises at least one relatively rigid longitudinal element (2) of a suitable material, such as plastic, having distal (3) and proximal (4) ends and a throughbore (7), thereby defining a tube with inner (6) and outer (10) walls and a longitudinal axis (5). Preferably the device is provided with a second longitudinal element (2a), mounted inside the throughbore (7) of the first longitudinal element (2), which second longitudinal element (2a) is also provided with a second throughbore (7a), inner (6a) and outer (10a) walls, and second distal (3a) and proximal (4a) ends, the second distal end (3a) extending beyond the first distal end (3) of the first longitudinal element (2).

The preferred device of FIG. 1 is also equipped with an inflatable element (8) which tightly surrounds at least a distal part of the outer or inner walls (6, 10) of the longitudinal element. The inflatable element (8) may be made of any suitable material, but preferably of a medical grade material, such as PVC, or rubber. The inflatable element can be made of semi-elastic material, as some stretch is considered desirable in permitting the inflatable element to conform to the space available in the body, or of inelastic material. In any event, the inflatable element should not stretch to the point that damage to the peritoneum or an underlying organ occurs. The inflatable element may be in sealing engagement with the outer or inner walls (6,10) of the longitudinal element (2). In the case of engagement with the inner wall (6), the inflatable element can be wrapped around an end of the longitudinal element and affixed, such as by gluing, heat sealing, ultrasonic welding or the like, to the inner wall (6). In the particularly preferred embodiment represented in FIG. 1, the inflatable element (8) tightly surrounds both the outer wall (10) of the first longitudinal element (2) at a proximal part (9) thereof, and the outer wall (10a) of the second longitudinal element (2a) at a distal part thereof (9a).

The inflatable element (8) has substantially two configurations, the importance of which will become evident from the following description. As shown in FIG. 1, it can adopt a first, flattened deflated configuration for its introduction, having the contour shown in FIG. 1. This flattened configuration effectively allows for the device to be introduced into a small incision, as is commonly carried out in laparoscopic surgery. To ease introduction and subsequent inflation the inflatable element (8) may be rolled up on either side of the longitudinal axis (5), such that it unravels inside the body when inflated with an inflating fluid such as air.

The inflatable element can also adopt a second substantially planar inflated configuration along a median plane which substantially corresponds to the plane of separation that exists between the peritoneum and the overlying abdominal wall. The inflation of the inflatable element (8) from the deflated to the inflated state, when placed inside the preperitoneal region according to the present invention, and as will be described more thoroughly further on, provides a separating force perpendicular to and on both sides of the above-mentioned median plane, thereby causing the peritoneum to separate from the overlying abdominal wall, to create a preperitoneal workspace.

Figure 2:
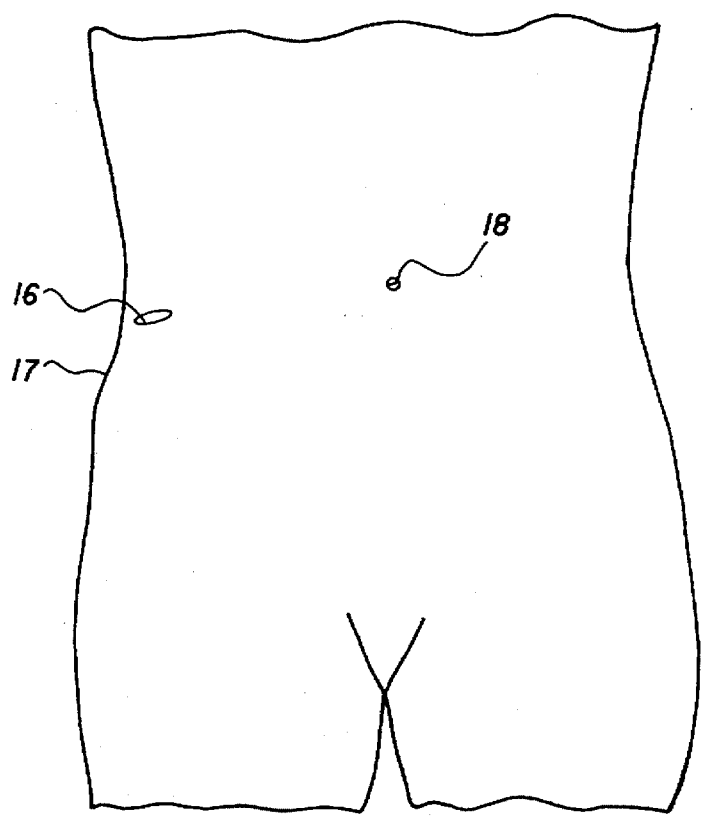
FIG. 2 is a schematic representation of the lower thorax and abdomen of the human body, indicating the site of first incision in the method according to the present invention.
Figure 5:
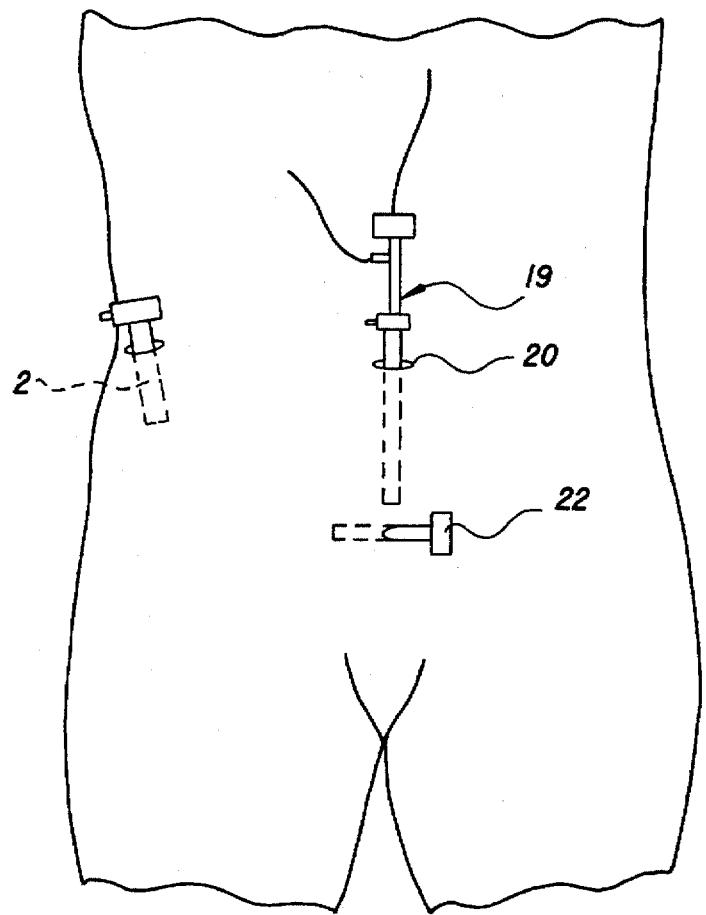
FIG. 5 schematically represents the positions of the surgical instruments, after insertion of another trocar into the preperitoneal workspace above the symphysis pubis.

Accordingly with similar inflatable elements known from the prior art, the inflatable element (8) is disposed around the longitudinal axis (5), and along said at least longitudinal element (2) over a predetermined distance. However, the inflatable element (8) of the invention differs from those associated with the devices of the prior art in that it has a generally asymmetrical shape or contour with respect to the general axis (5). This shape is defined by the element having, on one side of the axis (5), a relatively large and substantially flat surface (13) area, and on the other side of said axis (5), a relatively small and substantially flat surface (15) area, whereby said surface areas (13, 15) correspond to the space available in the body after insertion of the device (1) via an incision (16) made at the anterosuperior iliac crest (17) (cf. FIG. 2). Indeed, the asymmetric shape of the inflatable element of the device according to the present invention enables the surgeon to create a preperitoneal workspace in essentially one separating step, thereby avoiding any need for tunnelling or a series of inflating and separating steps as known from prior art devices.

The inflatable element is typically 12 cm long (along the longitudinal axis (5)), 15 cm across and 7 cm deep. Thus the inflatable element will generally be sized within the ranges of 8-15 cm long, 10-20 cm across and 5-10 cm deep. The inflatable element typically has a relatively small surface area extending $1/5$ of the total distance across and a relatively large surface area extending $4/5$ of the total distance across, the inflatable element, with the longitudinal axis (5) thereinbetween. Broadly, this proportion of the distance across the inflatable member can vary from $1/10$ to $1/3$ for the relatively small surface area and from $2/3$ to $9/10$ for the relatively large surface area. The inflatable member when inflated is arcuate in overhead profile, as shown in FIG. 1. The shape is roughly in the form of a kidney, or the shape could be described as generally triangular with rounded corners.

Inflation of the inflatable element (8) is achieved by providing inflating means (11) which communicate therewith and may be integrated into the device or separate therefrom. The inflating means (11) may comprise any suitable means which establishes a connection from an inflating fluid source to said inflatable element (8). In the presently preferred embodiment, the inflating means comprises first tap means (26) disposed in the vicinity of the proximal end (4) of said first longitudinal element (2), said tap means (26) communicating most preferably with the inflatable element (8) via the first throughbore (7).

The tap means (26), as represented by FIG. 1, and in accordance with the preferred embodiment of the invention, is provided with an entry port (27) and an exit port (28), between which is disposed a one way deformable membrane (29), which elastically deforms, under pressure from an external fluid source introduced via the entry port (27), in the direction of the exit port (28), thereby permitting inflating fluid to pass into the first longitudinal element (2), said membrane (29) being non deformable in the reverse direction, thereby preventing said insufflated fluid from escaping via the tap means (26).

In addition to the inflation means (11) represented in FIG. 1, the device also comprises insufflation means (11a), which enable a preperitoneal pneumoperitoneum to be created after the inflatable element (8) has been deflated, by injection of insufflating fluid into the preperitoneal cavity formed thereby. In the preferred embodiment of FIG. 1, the insufflation means (11a) is also disposed in the vicinity of the proximal end (4.4a) of the longitudinal elements (2, 2a) and comprises second tap means (26a), also equipped with entry (27a) and exit ports (28a) and a one way deformable membrane (29a), as for the inflation means (11). In particular, the insufflation means (11a) communicates with the second throughbore (7a) of the second longitudinal element (2a), that is to say, the inner of the two longitudinal elements (2, 2a).

Figure 6:
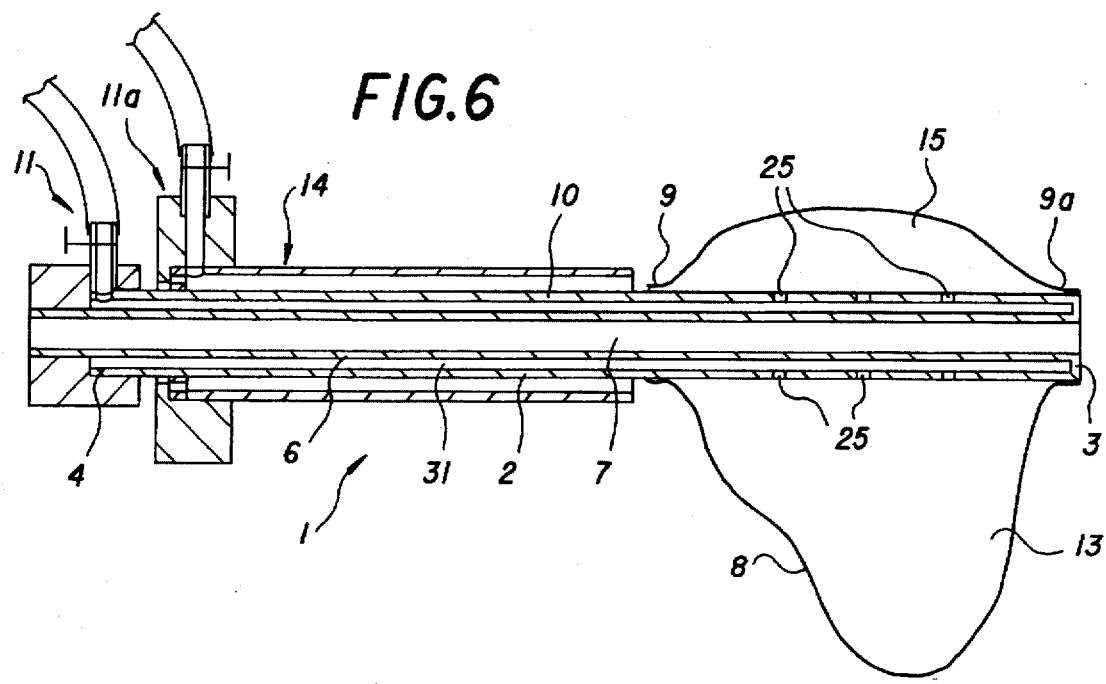
FIG. 6 represents a longitudinal cross section of a variant on the preferred device according to the present invention.

A preferred variant on the above embodiment may also be used in accordance with the present invention and is represented by FIG. 6. This second preferred embodiment is comprised by the device (1) as essentially described above, with the difference that the inflatable element (8) tightly surrounds the outer wall (10) of only one longitudinal element (2), at distal and proximal parts (9, 9a) thereof. The longitudinal element (2) is formed of cylindrical tubing with a hollow interior between its inner and outer walls (6, 10), forming an inflating passageway (31), and communicating with the inflatable element (8) via exit means (25), for example through holes or ports, formed in the outer wall (10). The device according to this preferred embodiment also comprises introducing means (14), surrounding the at least one longitudinal element (2), and equipped with insufflation means (11a). It is to be noted that the details concerning the inflation and insufflation means (11, 11a) have been omitted in FIG. 6 for the sake of clarity, but may be substantially the same as those described for the first preferred embodiment.

Figure 7:
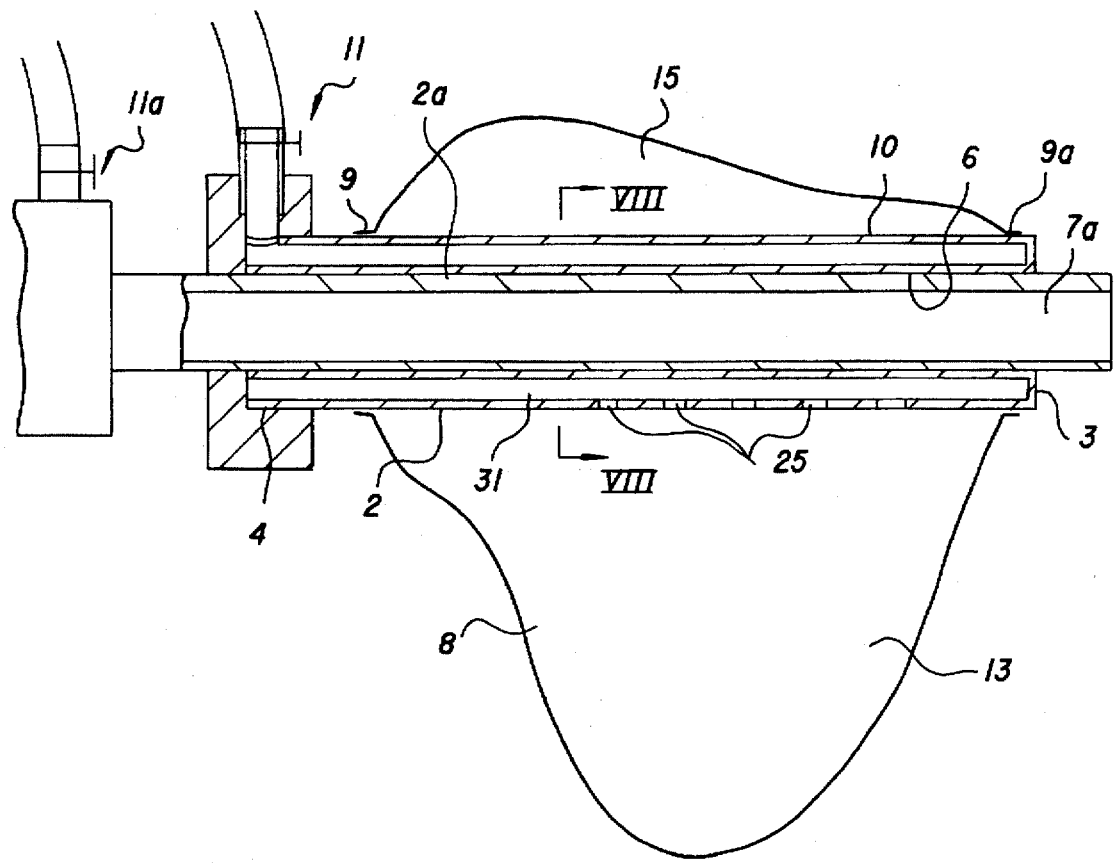
FIG. 7 represents a longitudinal cross-sectional view of yet another variant on the device according to the invention, similar to FIG. 1.
Figure 8:
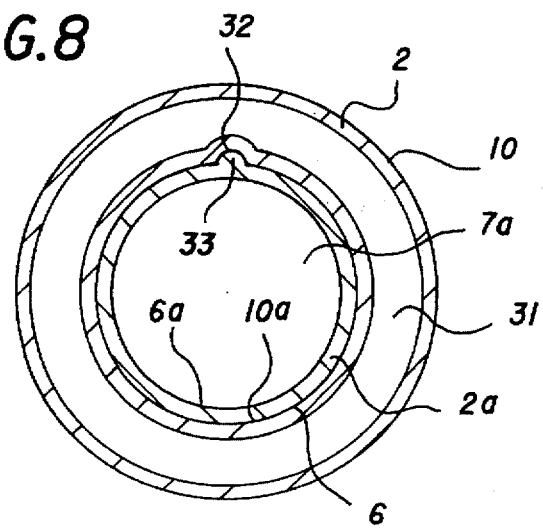
FIG. 8 represents a transverse cross-sectional 5 view of the device illustrated in FIG. 7, along the line VIII—VIII.

FIGS. 7 and 8 schematically represent yet another preferred embodiment of the device according to the present invention. In FIG. 7, the device is substantially the same as that in FIG. 1, and will therefore only be described in relation to the differences between the two embodiments. In this embodiment the longitudinal element (2) is provided with a groove (32) (not shown in FIG. 7) on the inner wall (6) extending substantially from the distal end (3) towards the proximal end (4) of the element (2), which groove (32) is designed to fit and retain a corresponding longitudinal rib (33) (not shown) provided on the outer wall (10a) of the second longitudinal element (2a), the groove (32) and the rib (33) preventing rotation of the two longitudinal elements (2, 2a) when the latter engages the former. FIG. 8 shows a cross-sectional view of FIG. 7 along the line VIII—VIII, wherein the groove (32) and rib (33) are clearly visible. The advantage of this particular arrangement is that the surgeon does not have to maneuver the inflatable element (8) into the correct position, as the outer longitudinal element (2) is prevented from rotating by the cooperation of the groove (32) and the rib (33). Furthermore, the outer longitudinal element (2) comprising the inflatable element (8) can be manufactured so as to be disposable, for example by extrusion moulding, while the inner longitudinal element (2a) can be a trocar made of metal, and be resterilised. This enables a significant reduction in the complexities and cost of manufacturing of the device, since only one mould is necessary.

The device according to the present invention may also be provided with other technical features in order to increase its usability and field of application. For example, the device may be provided with an opening (23) for the insertion of laparoscopic instruments at the proximal end (4) of the at least one longitudinal element (2), said opening defining a housing (31) which is closed by sealing means (12) comprising a moveable seal (30) disposed in the vicinity of the opening (23).

The method of use of the device, for the creation of a preperitoneal workspace in inguinal hernia repair 10 will now be explained with reference to FIGS. 2 to 5. A device as previously described is fitted with a laparoscope (19). The longitudinal elements (2, 2a) are in the form of a trocar, and the inflatable element (8) in the form of a balloon affixed to the central part of the trocar tube. A first incision (16) is made at the anterosuperior iliac spine (17), homolateral to the hernial site. The preperitoneal region is directly engaged and separation commenced by insertion of the surgeon's finger. The device is inserted horizontally, the trocar oriented so as to ensure that the inflatable element will expand more in the direction of the opposite facing iliac spine, i.e. the larger surface area part (13) of the balloon is placed facing towards the umbilicus (18). The separation of the peritoneum is carried out with the aid of the laparoscope (19), by inflation of the inflatable element (8), which is deployed towards said umbilicus and the epigastric vessels (cf. FIG. 3). The inflatable element or balloon (8) is thereafter deflated and left in place. The space thus formed is maintained artificially by insufflation of carbon dioxide gas. A second horizontal incision (20) is then made two centimeters underneath the umbilicus (18), the anterior sheath of the rectus muscles incised transversely, and retracted laterally. A lifting trocar (21) is inserted in this incision (20) and the laparoscope (19) inserted therein (cf. FIG. 4). Following that, a third trocar is introduced at about 4 to 5 centimeters above the pubis enabling nearer access to the hernial site and permitting the insertion of other instruments (cf. FIG. 5). The hernial repair is thereafter carried out by known procedure, usually involving the placing and stapling of a prosthetic patch at the hernial site after dissection and reduction of the hernial sac.

I claim:

1. A laparoscopic surgical separating device for separating a peritoneum of a patient from an overlying abdominal wall of the patient to permit access to a preperitoneal operative site in the patient for use in preperitoneal laparoscopic inguinal hernia repair in the patient, said device comprising at least a first longitudinal element having first distal and proximal ends, a longitudinal axis, an exterior wall and an interior wall, said exterior wall and said interior wall together defining at least a first throughbore;

an inflatable element in sealing engagement with at least a distal part of the exterior or interior wall of the first longitudinal element;

inflating means communicating with the inflatable element for inflating the inflatable element;

the inflatable element having a first, flattened deflated configuration suitable for insertion into a preperitoneal region of the patient, and a second, substantially planar inflated configuration along a median plane for providing a separating force perpendicular to the median plane such that when the inflatable element is inflated, said inflatable element has a front substantially planar surface and a rear substantially planar surface, said front substantially planar surface being substantially parallel to said rear substantially planar surface, said median plane and said longitudinal axis, and said front substantially planar surface is spaced apart from said rear substantially planar surface by a spacing distance perpendicular to said longitudinal axis and said front and rear substantially planar surfaces, and when the inflatable element is deflated and flattened, said front and rear substantially planar surfaces have substantially the same dimensions as when the inflatable element is inflated, and the from and rear substantially planar surfaces are in contact with each other, so that if the inflatable element is inflated in the preperitoneal region of the patient, the inflatable element separates the peritoneum and the overlying abdominal wall to create a preperitoneal workspace, the inflatable element being disposed around a portion of the longitudinal axis and along said first longitudinal element over a predetermined distance, the inflatable element having a generally asymmetrical shape such that the inflatable element has a first substantially flat surface on one side of the longitudinal axis and a second substantially flat surface on the other side of the longitudinal axis, said first substantially flat surface having a larger surface area than said second substantially flat surface, said first and second surfaces corresponding to a space available in the body of the patient after insertion of the device through an incision made at an antero-superior iliac crest of the patient.

2. The device of claim 1, further including insufflation means for passing an insufflating fluid through said first throughbore, the inflating means and the insufflating means being disposed in the vicinity of the proximal end of the first longitudinal element, the inflating means comprising a first tap device and the insufflation means comprising a second tap device.

3. The device of claim 2, wherein the inflating means communicates with the inflatable element via the first throughbore, and the insufflation means communicates with a second throughbore defined by an inside surface of said interior wall.

4. The device of claim 3, wherein the first and second tap devices each include an entry port and an exit port between which a one way deformable membrane is disposed, each said membrane elastically deforming, under pressure from an external fluid source introduced via the entry port, in a first direction toward the exit port to permit inflating fluid and insufflating fluid respectively to pass into the respective first and second throughbores, said membranes each being non deformable in a second direction opposite said first direction to prevent the inflating fluid and the insufflating fluid from escaping via the tap devices.

5. The device of claim 1, wherein the inflatable element is in sealing engagement with the exterior wall of the first longitudinal element at distal and proximate parts thereof.

6. The device of claim 1, wherein the first longitudinal element comprises a cylindrical tube having a hollow interior forming an inflating passageway between its outside and inside walls, the inflating passageway communicating with the inflating element via exit ports formed in the exterior wall.

7. The device of claim 1, further including an opening for accommodating insertion of laparoscopic instruments, said opening located at the proximal end of the first longitudinal element, the opening defining a housing, and moveable seal means disposed in a vicinity of the opening for sealing the housing.

8. The device of claim 1, further including passage means surrounding a portion of the first longitudinal element for passing insufflation fluid therethrough, said passage means being operatively associated with an insufflation means.

9. The device of claim 1, wherein the inflatable element is in sealing engagement with the exterior wall at both a distal and proximate part thereof, the exterior wall being provided with a longitudinal groove on an inner surface of said exterior wall, said groove extending substantially from the distal end towards the proximal end of the exterior wall, a mating longitudinal rib provided on an outer surface of the interior wall, the groove and the rib cooperating to prevent relative rotation of the first and second longitudinal elements when the rib engages the groove.

10. A laparoscopic surgical separating device for separating a peritoneum of a patient from an overlying abdominal wall of the patient to permit access to a preperitoneal operative site in the patient for use in preperitoneal laparoscopic inguinal hernia repair in the patient, said device comprising at least a first longitudinal element having first distal and proximal ends, a longitudinal axis, an exterior wall and an interior wall, said exterior wall and said interior wall together defining at least a first throughbore;

inflatable element means disposed around the longitudinal axis and along the first longitudinal element over a predetermined distance for changing in shape from a first, flattened deflated configuration, which permits insertion of the device through an incision to enter a preperitoneal region of the patient, to a second, substantially planar inflated configuration having a medial plane to provide a separating force perpendicular to the medial plane during inflation to cause separation of the peritoneum and the overlying abdominal wall to create a preperitoneal operating workspace, the inflatable element means having a generally asymmetrical shape with a first substantially flat surface area means on one side of the longitudinal axis and parallel to it and a second substantially flat surface area means on the opposite side of the longitudinal axis and parallel to a said first substantially flat surface having a larger surface area than said second substantially flat surface, said first and second surface area means for substantially filling a space available in the body of the patient after insertion of the device through an incision made at an antero-superior iliac crest of the patient and for exerting said separating force to separate the peritoneum and the overlying abdominal wall; and inflating means communicating with the inflatable element means for inflating the inflatable element.

11. A method for separating a peritoneum of a patient from an overlying abdominal wall of the patient to create a preperitoneal workspace permitting access to a preperitoneal operative site, comprising:

a) making a first traversing incision in the abdominal wall of the patient as far as an anterior surface of the peritoneum of the patient, in the vicinity of an antero-superior iliac crest, homolateral to a hernia to be repaired;

b) introducing a separating device generally horizontally into the incision to enter a preperitoneal region of the patient;

c) expanding the separating device, with the expansion being greater towards an opposite facing side of a body of the patient than toward a side of the introduction, to separate the peritoneum from the overlying abdominal wall by the effect of an expanding force acting perpendicular to a plane of separation between the peritoneum and the overlying abdominal wall, to create a preperitoneal cavity;

contracting the introduced separating device, and insufflating the preperitoneal cavity with insufflating fluid to create a preperitoneal pneumoperitoneum, thereby creating an operative workspace.

12. Method of claim 11, wherein the method is a method of laparoscopically repairing an inguinal hernia, the method further comprising the steps:

e) making a second traversing incision infraumbilically, through an anterior rectus sheath of the patient, and retracting rectus abdominis muscles of the patient;

f) introducing a trocar equipped with a laparoscope through the second incision into the preperitoneal workspace;

g) introducing a third trocar into the preperitoneal workspace above a symphysis pubis of the patient; and h) dissecting and reducing the hernia, and placing a repairing prosthetic patch at a site of said hernia.

13. A laparoscopic surgical separating device for separating a peritoneum of a patient from an overlying abdominal wall of the patient to permit access to a preperitoneal operative site for use in preperitoneal laparoscopic inguinal hernia repair in the patient, said device comprising at least a first longitudinal element having first distal and proximal ends, a longitudinal axis, an exterior wall and an interior wall, said exterior wall and said interior wall together defining at least a first throughbore;

an inflatable element in sealing engagement with at least a first location around a periphery of said exterior wall and a second location around a periphery of said interior wall, said first location and said second location being spaced from each other along said longitudinal axis;

inflating means communicating with the inflatable element for inflating the inflatable element;

the inflatable element having a first, flattened deflated configuration suitable for insertion into a preperitoneal region of the patient, and a second, substantially planar inflated configuration along a median plane for providing a separating force perpendicular to the median plane such that when the inflatable element is inflated, said inflatable element has a front substantially planar surface and a rear substantially planar surface, said from substantially planar surface being substantially parallel to said rear substantially planar surface, said median plane and said longitudinal axis, and said front substantially planar surface is spaced apart from said rear substantially planar surface by a spacing distance perpendicular to said longitudinal axis and said front and rear substantially planar surfaces, and when the inflatable element is deflated and flattened, said front and rear substantially planar surfaces have substantially the same dimensions as when the inflatable element is inflated, and the front and rear substantially planar surfaces are in contact with each other, so that if the inflatable element is inflated in a preperitoneal region of the patient, the inflatable element separates the peritoneum and the overlying abdominal wall to create a preperitoneal workspace, the inflatable element being disposed around a portion of the longitudinal axis and along said at least one longitudinal element over a predetermined distance, the inflatable element having a generally asymmetrical shape such that the inflatable element has a first substantially flat surface on one side of the longitudinal axis and a second substantially flat surface on the other side of the longitudinal axis, said first substantially flat surface having a larger surface area than said second substantially flat surface, said first and second surfaces corresponding to a space available in the body of the patient after insertion of the device through an incision made at an antero-superior iliac crest of the patient.

14. A laparoscopic surgical separating device for separating a peritoneum of a patient from an overlying abdominal wall of the patient to permit access to a preperitoneal operative site for use in preperitoneal laparoscopic inguinal hernia repair in the patient, said device comprising at least a first longitudinal element having first distal and proximal ends, a longitudinal axis, an exterior wall and an interior wall, said exterior wall and said interior wall together defining at least a first throughbore;

an inflatable element in sealing engagement with at least a first location around a periphery of said exterior wall and a second location around a periphery of said exterior wall, said first location and said second location being spaced from each other along said longitudinal axis;

inflating means communicating with the inflatable element for inflating the inflatable element;

the inflatable element having a first, flattened deflated configuration suitable for insertion into a preperitoneal region of the patient, and a second, substantially planar inflated configuration along a median plane for providing a separating force perpendicular to the median plane such that when the inflatable element is inflated, said inflatable element has a front substantially planar surface and a rear substantially planar surface, said front substantially planar surface being substantially parallel to said rear substantially planar surface, said median plane and said longitudinal axis, and said front substantially planar surface is spaced apart from said rear substantially planar surface by a spacing distance perpendicular to said longitudinal axis and said front and rear substantially planar surfaces, and when the inflatable element is deflated and flattened, said front and rear substantially planar surfaces have substantially the same dimensions as when the inflatable element is inflated, and the front and rear substantially planar surfaces are in contact with each other, so that if the inflatable element is inflated in a preperitoneal region of the patient, the inflatable element separates the peritoneum and the overlying abdominal wall to create a preperitoneal workspace, the inflatable element being disposed around a portion of the longitudinal axis and along said at least one longitudinal element over a predetermined distance, the inflatable element having a generally asymmetrical shape such that the inflatable element has a first substantially flat surface on one side of the longitudinal axis and a second substantially flat surface on the other side of the longitudinal axis, said first substantially flat surface having a larger surface area than said second substantially flat surface, said first and second surfaces corresponding to a space available in the body of the patient after insertion of the device through an incision made at an antero-superior iliac crest of the patient.

15. A laparoscopic surgical separating device for separating a peritoneum of a patient from an overlying abdominal wall of the patient to permit access to a preperitoneal operative site for use in preperitoneal laparoscopic inguinal hernia repair in the patient, said device comprising at least a first longitudinal element having first distal and proximal ends, a longitudinal axis, an exterior wall and an interior wall, said exterior wall and said interior wall together defining at least a first throughbore;

an inflatable element in sealing engagement with at least a first location around a periphery of said exterior wall and a second location around a periphery of said interior wall, said first location and said second location being spaced from each other along said longitudinal axis;

inflating means communicating with the inflatable element for inflating the inflatable element;

the inflatable element having a first, flattened deflated configuration suitable for insertion into a preperitoneal region of the patient, and a second, substantially planar inflated configuration along a median plane for providing a separating force perpendicular to the median plane when the inflatable element is inflated in a preperitoneal region of the patient to separate the peritoneum and the overlying abdominal wall to create a preperitoneal workspace, the inflatable element being disposed around a portion of the longitudinal axis and along said first longitudinal element over a predetermined distance, the inflatable element having a generally asymmetrical shape such that the inflatable element has a first substantially flat surface on one side of the longitudinal axis and parallel to it and a second substantially flat surface on the other side of the longitudinal axis and parallel to it, said first substantially flat surface having a larger surface area than said second substantially flat surface, said first and second surfaces corresponding to a space available in a body of the patient after insertion of the device through an incision made at an anterosuperior iliac crest of the patient.

16. A laparoscopic surgical separating device for separating a peritoneum of a patient from an overlying abdominal wall of the patient to permit access to a preperitoneal operative site for use in preperitoneal laparoscopic inguinal hernia repair in the patient, said device comprising at least a first longitudinal element having first distal and proximal ends, a longitudinal axis, an exterior wall and an interior wall, said exterior wall and said interior wall together defining at least a first throughbore;

an inflatable element in sealing engagement with at least a first location around a periphery of said exterior wall and a second location around a periphery of said exterior wall, said first location and said second location being spaced from each other along said longitudinal axis;

inflating means communicating with the inflatable element for inflating the inflatable element;

the inflatable element having a first, flattened deflated configuration suitable for insertion into a preperitoneal region of the patient, and a second, substantially planar inflated configuration along a median plane for providing a separating force perpendicular to the median plane when the inflatable element is inflated in a preperitoneal region of the patient to separate the peritoneum and the overlying abdominal wall to create a preperitoneal workspace, the inflatable element being disposed around a portion of the longitudinal axis and along said first longitudinal element over a predetermined distance, the inflatable element having a generally asymmetrical shape such that the inflatable element has a first substantially flat surface on one side of the longitudinal axis and parallel to it and a second substantially flat surface on the other side of the longitudinal axis and parallel to it, said first substantially flat surface having a larger surface area than said second substantially flat surface, said first and second surfaces corresponding to a space available in a body of the patient after insertion of the device through an incision made at an antero-superior iliac crest of the patient.

17. A method for separating a peritoneum of a patient from an overlying abdominal wall of the patient to create a preperitoneal workspace permitting access to a preperitoneal operative site, comprising:

a) making a first traversing incision in the abdominal wall of the patient as far as an anterior surface of a peritoneum of the patient, in the vicinity of an antero-superior iliac crest, homolateral to a hernia to be repaired;

b) introducing a separating device as recited in claim 1 generally horizontally into the incision to enter a preperitoneal region of the patient;

c) expanding the separating device, with the expansion being greater towards an opposite facing side of a body of the patient than toward a side of the introduction, to separate the peritoneum from the overlying abdominal wall by the effect of an expanding force acting perpendicular to a plane of separation between the peritoneum and the overlying abdominal wall, to create a preperitoneal cavity;

contracting the introduced separating device, and insufflating the preperitoneal cavity with insufflating fluid to create a preperitoneal pneumoperitoneum, thereby creating an operative workspace.

* * * * *